(12) United States Patent
Kil

(10) Patent No.: US 12,427,138 B2
(45) Date of Patent: Sep. 30, 2025

(54) TREATMENT OF MENIERE'S DISEASE

(71) Applicant: SOUND PHARMACEUTICALS INCORPORATED, Seattle, WA (US)

(72) Inventor: Jonathan Kil, Seattle, WA (US)

(73) Assignee: SOUND PHARMACEUTICALS INCORPORATED, Seattle, WA (US)

(*) Notice: Subject to any disclaimer, the term of this patent is extended or adjusted under 35 U.S.C. 154(b) by 435 days.

(21) Appl. No.: 16/300,935

(22) PCT Filed: May 18, 2017

(86) PCT No.: PCT/US2017/033379
§ 371 (c)(1),
(2) Date: Nov. 12, 2018

(87) PCT Pub. No.: WO2017/201318
PCT Pub. Date: Nov. 23, 2017

(65) Prior Publication Data
US 2020/0261417 A1   Aug. 20, 2020

Related U.S. Application Data

(60) Provisional application No. 62/338,443, filed on May 18, 2016.

(51) Int. Cl.
| | | |
|---|---|---|
| A61K 31/41 | (2006.01) |
| A61K 9/48 | (2006.01) |
| A61K 31/167 | (2006.01) |
| A61K 31/197 | (2006.01) |
| A61K 31/221 | (2006.01) |
| A61K 31/426 | (2006.01) |
| A61K 31/427 | (2006.01) |
| A61K 45/06 | (2006.01) |
| A61P 27/16 | (2006.01) |

(52) U.S. Cl.
CPC ........... *A61K 31/41* (2013.01); *A61K 9/48* (2013.01); *A61K 31/167* (2013.01); *A61K 31/197* (2013.01); *A61K 31/221* (2013.01); *A61K 31/426* (2013.01); *A61K 31/427* (2013.01); *A61K 45/06* (2013.01); *A61P 27/16* (2018.01)

(58) Field of Classification Search
CPC .... A61K 31/41; A61K 31/167; A61K 31/197; A61K 31/221; A61K 31/426; A61K 31/427; A61P 27/16
See application file for complete search history.

(56) References Cited

U.S. PATENT DOCUMENTS

| | | | | |
|---|---|---|---|---|
| 6,815,434 B2 * | 11/2004 | Kil | ...................... | A61K 31/519 514/58 |
| 2003/0162747 A1 * | 8/2003 | Kil | ...................... | A61K 31/195 514/58 |
| 2004/0220145 A1 | 11/2004 | Kil et al. | | |
| 2010/0022458 A1 | 1/2010 | Kopke et al. | | |
| 2015/0374779 A1 | 12/2015 | Meyer | | |

FOREIGN PATENT DOCUMENTS

| | | |
|---|---|---|
| CN | 102526734 A | 7/2012 |
| JP | 2005-516028 A | 6/2005 |
| WO | WO-2007/044700 A2 | 4/2007 |
| WO | WO-2009/140382 A2 | 11/2009 |
| WO | WO-2012/106654 A1 | 2/2011 |
| WO | WO-2016/044314 A1 | 3/2016 |
| WO | WO-2018/005830 A1 | 1/2018 |

OTHER PUBLICATIONS

NCT02603081 Study to evaluate SPI-1005 in Adults with Meniere disease, Clinicaltrials.gov archive Dec. 10, 2015, https://clinicaltrials.gov/ct2/history/NCT02603081?A=2&B=2&C=merged, accessed Aug. 8, 2021.*
Herraiz et al. Eur Arch Otorhinolaryngol 2006, 263, 504-509.*
Green et al. The Laryngoscope 2007, 117, 1622-1628.*
PCT International Search Report & Written Opinion for International Application No. PCT/US2017/033379, dated Oct. 20, 2017, 15 Pages.
Botta, M., "Sound Pharmaceuticals, Oxford Collaborate on Bipolar Treatment," Drug Development; Mar. 10, 2016, 6 Pages, Can be retrieved at <URL:https://www.pharmpro.com/news/2016/03/sound-pharmaceuticals-oxford-collaborate-bipolar-treatment>.
Botta, M., "Sound Pharmaceuticals, Oxford Collaborate on Bipolar Treatment," Drug Development, Mar. 10, 2016, 6 pages.
Chen, G. et al., "Hearing loss: what's in the pipeline," Drugs of the Future, 2011, vol. 36, No. 3, pp. 209-227.
Debashree, M. et al., "Early Investigational drugs for hearing loss," Taylor & Francis, Sep. 22, 2014, vol. 24, No. 2, pp. 201-207.
European Patent Office, Partial Supplementary European Search Report, European Patent Application No. 17800188.9, Dec. 19, 2019, 18 pages.
Mishra, B. et al., "Horseradish peroxidase inhibition and antioxidant activity of Ebselen and related organoselenium compounds," Bioorganic & Medicinal Chemistry Letters, Science Direct, 2006, vol. 16, pp. 5334-5338.
Morgenstern, R. et al., "Determination of the relative contributions of the diselenide and selenol forms of Ebselen in the mechanism of its glutathione peroxidase-like activity,"Chem.-Biol. Interactions, 1992, vol. 84, pp. 77-84.
Dolgin, E. et al., "Sound Medicine," Nature Medicine, vol. 18, No. 5, May 2012, pp. 642-645.
European Patent Office, Extended European Search Report and Opinion, EP Patent Application No. 17800188.9, Aug. 13, 2020, 21 pages.

(Continued)

*Primary Examiner* — Irina Neagu
(74) *Attorney, Agent, or Firm* — Fenwick & West LLP

(57) ABSTRACT

Disclosed herein are novel methods and compositions for treating MD and/or endolymphatic hydrops. The composition comprises ebselen and optionally one or more a glutathione peroxidase (GPx) modulator or mimic compounds and/or one or more prescription diuretic compounds. Also disclosed are methods of increasing GPx activity and reducing free radical species and cochlear or vestibular inflammation in a subject.

29 Claims, 3 Drawing Sheets

(56) References Cited

OTHER PUBLICATIONS

Kil, J. et al., "Ebselen treatment reduces noise induced hearing loss via the mimicry and induction of glutathione peroxidase," Hearing Research, vol. 226, Oct. 6, 2006, pp. 44-51.
Lorito, G. et al., "Dose-dependent protection on cisplatin-induced ototoxicity—an electrophysiological study on the effect of three antioxidants in the Sprague-Dawley rat animal mode," Med Sci Monit 17(8), Aug. 1, 2011, pp. BR179-BR186.
Pourbakht, A. et al., "Ebselen attenuates cochlear damage caused by acoustic trauma," Hearing Research, vol. 181, 2003, pp. 100-108.
Bosch-Morell, F. et al., "Role of oxygen and nitrogen species in experimental uveitis: anti-inflammatory activity of the synthetic antioxidant ebselen," Free Radic Biol Med, 33(1), Oct. 2002, pp. 669-675.
Duracinsky, M. et al., "Literature Review of Questionnaires Assessing Vertigo and Dizziness, and Their Impact on Patients' Quality of Life," Value in Health, Jul. 2007, 10(4), p. 273-284.
Frackell, K. et al., "Questionnaires to Measure Tinnitus Severity," ENT and Audiology News, vol. 22, No. 6, Feb. 2014, pp. 1-3.
Japan Patent Office, Office Action, JP Patent Application No. 2018-560665, Mar. 24, 2021, ten pages.
Korean Intellectual Property Administration, Office Action, KR Patent Application No. 10-2018-7036629, Jan. 21, 2022, 14 pages.
Lynch, E. D. et al., "Development of ebselen, a glutathione peroxidase mimic, for the prevention and treatment of noise-induced hearing loss," Seminars in Hearing, 30(01), Feb. 2009, pp. 47-55.
Saito, I. et al., "Neuroprotective Effect of an Antioxidant, Ebselen, in Patients with Delayed Neurological Deficits after Aneurysmal Subarachnoid Hemorrhage," Neurosurgery, vol. 42, Iss. 2, Feb. 1998, pp. 269-277.
Sound Pharmaceuticals, "Sound Pharmaceuticals and Oxford Collaborate on a New Treatment for Bipolar Disorder," Feb. 29, 2016, pp. 1-3, [Online] [Retrieved on Feb. 11, 2022] Retrieved from the Internet <URL: https://soundpharma.com/sound-pharmaceuticals-and-university-of-oxford-to-collaborate-on-psychiatric-diseases/#:~:text=Sound%20Pharmaceuticals%20(SPI)%20will%20collaborate,one%20percent%20of%20adults%20worldwide.>.
Stahle, J., "Medical treatment of fluctuant hearing loss in Meniere's disease," The American Journal of Otology 5(6), Oct. 1984, pp. 529-533.
Takumida, M. et al., "New medical treatment for Meniere's disease," Equilibrium Research 62(2), Apr. 2003, pp. 132-138.
Watanabe, Y., "Meniere's Disease Medical Care Recent Trends," Journal of Otolaryngology of Japan 115(9), Nov. 2012, pp. 866-869.
Wilson, R.H. et al., "The Words-in-Noise (WIN) Test with Multitalker Babble and Speech-Spectrum Noise Maskers," Journal of the American Academy of Audiology, vol. 18, Iss. 6, 2007, pp. 522-529.
Yamasoba, T. et al., "Ebselen prevents noise-induced excitotoxicity and temporary threshold shift," Neuroscience Letters, 380(3), 2005, pp. 234-238.
Basura, G. et al. "Clinical Practice Guideline: Meniere's Disease," American Academy of Otolaryngology, *Otolaryngology—Head and Neck Surgery*, vol. 162, Apr. 2020, 56 pages.
Goebel, J. et al. "2015 Equilibrium Committee Amendment to the 1995 AAO-HNS Guidelines for the Definition of Ménière's Disease," American Academy of Otolaryngology, *Otolaryngology—Head and Neck Surgery*, vol. 154, No. 3, Mar. 2016, 2 pages.

\* cited by examiner

| PHASE 1B MENIERE'S DISEASE RESULTS | | | | | |
|---|---|---|---|---|---|
| Subject | ≥10 dB Hearing Improvement | ≥10% WRT Improvement | ≥10 pts Tinnitus Reduction | 2 pt VRT Reduction | 2 pt VAS Reduction |
| 63 female | Yes (10-30) | Yes (20%) | No | No | Yes (11) |
| 62 female | Yes (10-15) | Yes (14%) | No | Yes (9 to 7) | No |
| 54 female | Yes (10) | Yes (50%) | Yes (12) | Yes (9 to 7) | Yes (6) |
| 55 male | Yes (15) | No | No | Yes (6 to 3) | No |
| 68 male | Yes (10-20) | No | No | Yes (2 to 0) | No |
| 56 male | No | No | No | No | Yes (7) |
| 50 male | No | No | No | No | No |
| 71 female* | No | No | Yes (53) | Yes (8 to 4) | No |
| Placebo (*) | | | | | |

FIG 1.

| PHASE 1B MENIERE'S DISEASE RESULTS | | | | | |
|---|---|---|---|---|---|
| Subject | ≥10 dB Hearing Improvement | ≥16% WNT Improvement | ≥20 pts TH Reduction | ≥5 pts TI Reduction | ≥5 pts VSS Reduction |
| 44 female | Yes (10) | Yes (20%) | No | Yes (10 to 8) | Yes (6) |
| 50 female | No | No | Yes (62) | Yes (8 to 0) | Yes (13) |
| 32 male | No | No | Yes (28) | Yes (7 to 4) | Yes (8) |
| 51 male | No | No | Yes (21) | Yes (7 to 3) | No |
| 48 male | Yes (20-35) | No | Yes (22) | Yes (9 to 7) | Yes (10) |
| 33 male | No | No | Yes (17) | Yes (8 to 4) | No |
| 60 female | No | No | No | Yes (9 to 7) | No |
| 66 male* | No | No | Yes (23) | Yes (9 to 6) | Yes (16) |
| 60 female* | No | No | No | No | No |
| 54 male* | No | No | Yes (24) | No | Yes (28) |
| Placebo (*) | | | | | |

FIG 2.

PHASE 1B MENIERE'S DISEASE RESULTS

| Subject | SC Hearing Improvement | SC VMIT Improvement (>100%) | SIONTR Reduction | T1 of 25 Reduction | Patient Reported SAVUR |
|---|---|---|---|---|---|
| 65 male | Yes (10-25) | Yes (120%) | Yes (38) | Yes (2 to 0) | Yes (33) |
| 48 male | Yes (15) | No | Yes (19) | Yes (6 to 4) | Yes (12) |
| 47 female | Yes (15-20) | Yes (113%) | No | No | No |
| 46 male | Yes (10-15) | No | No | No | No |
| 58 female | No | No | No | No | Yes (14) |
| 62 male | No | No | No | No | Yes (7) |
| 50 male* | No | No | No | No | No |
| 38 female* | No | No | No | No | No |
| Placebo (*) | | | | | |

FIG 3.

TREATMENT OF MENIERE'S DISEASE

BACKGROUND

Field of the Invention

The disclosure relates to compositions and methods useful for the treatment of Meniere's disease and/or endolymphatic hydrops.

Description of Related Art

Meniere's disease (MD) is defined as a triad of episodic vertigo, hearing loss and tinnitus. Aural pressure or fullness is often reported and most auditory and vestibular symptoms fluctuate in frequency and intensity. While the etiology of MD is unknown, it is related to endolymphatic hydrops. Endolymphatic hydrops is a swelling of the endolymphatic compartment of the inner ear. After an acute phase where vertigo is the most common feature, the chronic phase emerges, where hearing loss and tinnitus become the most common features, although disequilibrium is often reported. No drugs have been FDA approved to prevent or treat MD. Most MD patients are medically managed using a low-salt diet and/or a thiazide diuretic with limited success.

The present disclosure addresses the clinical need for a therapeutic to treat MD and/or endolymphatic hydrops.

SUMMARY

The inventors have discovered and show an improvement in several auditory and vestibular symptoms following treatment of human subjects presenting with MD and/or both idiopathic and non-idiopathic endolymphatic hydrops comprising administering an effective amount ebselen (SPI-1005) alone or in combination with one or more other glutathione peroxidase (GPx) modulator or mimic compounds and/or one or more prescription diuretic compounds.

The present disclosure provides novel glutathione. peroxidase (GPx) modulator or mimic compounds useful in pharmaceutical compositions, comprising ebselen alone or in combination with one or more of such glutathione peroxidase (GPx) modulator or mimic compounds and/or one or more prescription diuretic compounds, useful for treating, preventing, and/or ameliorating Meniere's disease and/or endolymphatic hydrops, methods of preparing such pharmaceutical compositions comprising ebselen or combinations including ebselen with novel glutathione peroxidase (GPx) modulator or mimic compounds and/or one or more prescription diuretic compounds, the pharmaceutical compositions comprising ebselen or combinations including ebselen with novel giutathione peroxidase (GPx) modulator or mimic compounds and/or one or more prescription diuretic compounds, as well as methods of treatment, preventing and/or ameliorating Meniere's disease and/or endolymphatic hydrops using these pharmaceutical compositions.

Some embodiments of the novel combination compositions comprise at least two compounds or pharmaceutically acceptable salts thereof, wherein the first compound is ebselen and the second compound is a glutathione peroxidase modulator or mimic compound.

Yet another aspect of the present disclose features a method of treating a subject suffering from or diagnosed with MD and/or endolymphatic hydrops comprising administering to the subject a therapeutically effective amount of a pharmaceutical composition comprising ebselen alone, or a combination of ebselen, one or more other glutathione peroxidase modulator or mimic compounds and optionally one or more prescription diuretic compounds. The therapeutically effective amount of each compound included in the novel combination can be from about 0.1 mg/day to about 5000 mg/day, respectively.

Another aspect of the present disclosure features a kit comprising any of the compositions described herein and instructions for use.

Another aspect of the present disclosure features a method for equalizing the pressure of the inner ear of a subject comprising administering a therapeutically effective amount of a composition comprising ebselen, and optionally one or more other glutathione peroxidase modulator or mimic compounds and/or one or more prescription diuretic compounds.

In yet another aspect, the present disclosure includes a method for reducing free radical species production and/or inflammation in the ear of a subject comprising administering a therapeutically effective amount of a composition comprising ebselen, and optionally one or more other glutathione peroxidase modulator or mimic compounds.

The present disclosure further features a process for making a pharmaceutical composition comprising admixing ebselen and any of the glutathione peroxidase modulator or mimic compounds or prescription diuretic compounds and one or more pharmaceutically acceptable carriers.

The disclosure provides for a pharmaceutical composition comprising ebselen and one or more other glutathione peroxidase (GPx) modulator or mimic compounds; or pharmaceutically acceptable salts or solvates thereof.

The disclosure provides for a composition wherein the one or more other glutathione peroxidase modulator or mimic compounds is present as one compound and is selected from the group consisting of 2,2'-diseleno-bis-β-cyclodextrin,

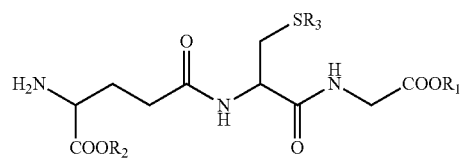

wherein
R$_1$ is H, methyl, ethyl, or isopropyl;
R$_2$ is H, or ethyl;
R$_3$ is H, acetyl, phenylacetyl,

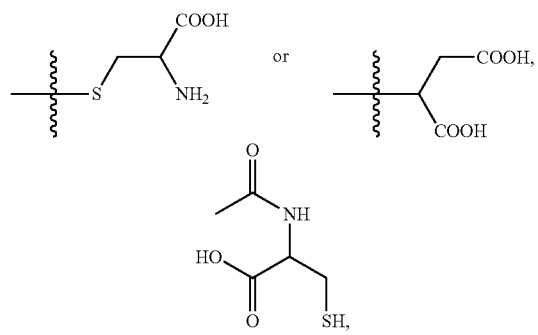

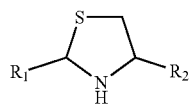

wherein
R₁ is H, oxo, methyl, ethyl, n-propyl, n-pentyl, phenyl, —(CHOH)$_n$CH$_2$OH or

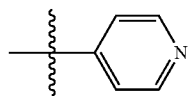

wherein n is 1-5; R₂ is H or —COOH,
and 6A,6B-diseleninic acid-6A',6B'-selenium bridged β-cyclodextrin.

The disclosure provides for a composition wherein the one or more other glutathione peroxidase modulator or mimic compounds is present as one compound and is 2,2'-diseleno-bis-β-cyclodextrin.

The disclosure provides for a composition wherein the composition comprises ebselen or a pharmaceutically acceptable salt or solvate thereof.

The disclosure provides for a composition wherein the composition further comprises one or more diuretic compounds.

The disclosure provides for a kit comprising the composition of any one of the embodiments described herein and instructions for use.

The disclosure provides for a method of treating, preventing, and/or ameliorating Meniere's disease in a subject comprising administering to a subject in need thereof an effective amount of a composition comprising ebselen, optionally in combination with a prescription diuretic compound.

The disclosure provides for a method of treating, preventing, and/or ameliorating Meniere's disease in a subject comprising administering to a subject in need thereof an effective amount of a composition comprising ebselen and one or more other glutathione peroxidase modulator or mimic compounds, optionally in combination with a prescription diuretic compound.

The disclosure provides for a method of treating, preventing, and/or ameliorating endolymphatic hydrops in a subject comprising administering to a subject in need thereof an effective amount of a composition comprising ebselen, optionally in combination with a prescription diuretic compound.

The disclosure provides for a method of treating, preventing, and/or ameliorating endolymphatic hydrops in a subject comprising administering to a subject in need thereof an effective amount of a composition comprising ebselen and one or more other glutathione peroxidase modulator or mimic compounds, optionally in combination with a prescription diuretic compound.

The disclosure provides for a method of any one of the embodiments described herein wherein the one or more other glutathione peroxidase modulator or mimic compounds is present as one compound and is selected from the group consisting of 2,2'-diseleno-bis-β-cyclodextrin,

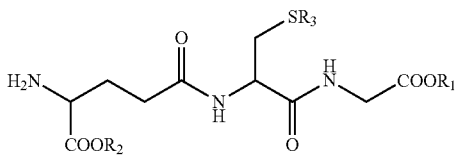

wherein
R₁ is H, methyl, ethyl, or isopropyl;
R₂ is H, or ethyl;
R₃ is H, acetyl, phenylacetyl,

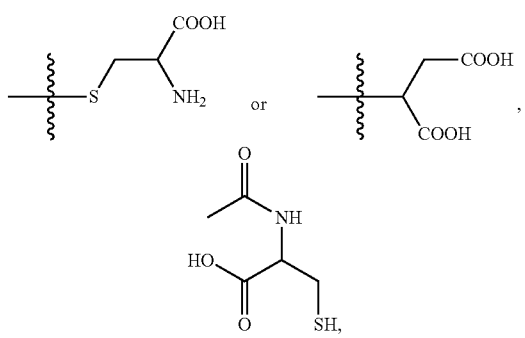

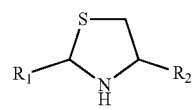

wherein
R₁ is H, oxo, methyl, ethyl, n-propyl, n-pentyl, phenyl, —(CHOH)$_n$CH$_2$OH or

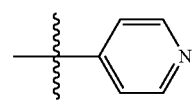

wherein n is 1-5; R₂ is H or —COOH,
and 6A,6B-diseleninic acid-6A',6B'-selenium bridged β-cyclodextrin.

The disclosure provides for a method of any one of the embodiments described herein wherein the one or more other glutathione peroxidase modulator or mimic compounds is present as one compound and is 2,2'-diseleno-bis-β-cyclodextrin.

The disclosure provides for a method of any one of the embodiments described herein wherein GPx activity is increased in a subject with Meniere's Disease or endolymphatic hydrops.

The disclosure provides for a method of any one of the embodiments described herein wherein the administration is oral.

The disclosure provides for a method of any one of the embodiments described herein wherein the efficacy of the method is measured by a technique that is selected from group consisting of pure-tone audiometry, speech discrimination testing, electrocochleography or magnetic resonance imaging.

The disclosure provides for a method of any one of the embodiments described herein wherein the treatment improves at least one of the subject's pure tone audiometry, speech discrimination test, electrocochleography or magnetic resonance imaging.

The disclosure provides for a method of any one of the embodiments described herein wherein the treatment increases at least one of the subject's tests score that is selected from group consisting of the Vertigo Symptoms Scale (VSS), Dizziness Handicap Inventory (DHI), Tinnitus Functional Index (TFI) or Tinnitus Handicap Inventory (THI).

The disclosure provides for a method of reducing free radical production and/or inflammation in the inner ear of a subject comprising administering to a subject in need thereof an effective amount of a composition comprising ebselen, and optionally one or more other glutathione peroxidase modulator or mimic compounds.

The disclosure provides for a method of any one of the embodiments described herein wherein the free radical is selected form group consisting of peroxynitrite, hydroperoxide anion, superoxide anion, nitric oxide, nitrotyrosine, and hydroxyl.

The disclosure provides for a method of equalizing pressure of the inner ear comprising administering to a subject in need thereof an effective amount of a composition comprising ebselen, and optionally one or more other glutathione peroxidase modulator or mimic compounds, and optionally a prescription diuretic.

The disclosure provides for a method of any one of the embodiments described herein wherein the subject has vertigo.

The disclosure provides for a method of any one of the embodiments described herein wherein the subject has dizziness.

The disclosure provides for a method of any one of the embodiments described herein wherein the subject has hearing loss.

The disclosure provides for a method of any one of the embodiments described herein wherein the subject has tinnitus.

The disclosure provides for a method of any one of the embodiments described herein wherein the inner ear pressure was/is demonstrated by electrocochleography or magnetic resonance imaging.

The disclosure provides for a method of any one of the embodiments described herein wherein the pharmaceutical composition further comprises one or more diuretic compounds, including prescription diuretic compounds.

The disclosure provides for a composition of any one of the embodiments described herein wherein the composition comprises ebselen and/or the dimer of ebselen, i.e. the compound represented by the formula:

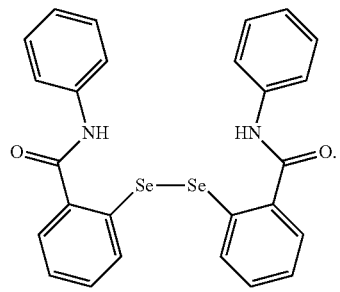

The Se—Se bond in this chemical structure is relatively weak. For example, it is known that the dimerization reaction from ebselen to form the Se—Se bond will occur spontaneously at lower pH environments. It is also known that the dimerization reaction is under thermodynamic control and is reversible. This means that ebselen can be made from and can be present in some equilibrium with the dimer form/compound. Accordingly, the inventors contemplate and it is herein disclosed that ebselen and this dimer compound are, for such purposes of this disclosure, equivalent. Thus, both active chemical species for the uses, kits, methods, and compositions disclosed herein. As such, it is herein contemplated that whenever referred to in this disclosure, the term ebselen (can be and) is replaceable with this dimer compound.

The disclosure provides for a method of any one of the embodiments described herein wherein the pharmaceutical composition comprises a compound which is the dimeric form of ebselen, i.e. the compound represented by the formula:

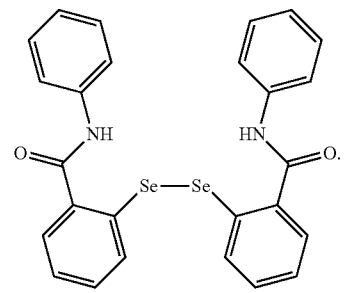 [SMILES: O=C(Nc1ccccc1)c1ccccc1[Se][Se]c1ccccc1C(=O)Nc1ccccc1]

Additional embodiments and their advantages will become apparent from the detailed discussion, schemes, examples, and claims below.

SUMMARY

BRIEF DESCRIPTION OF THE FIGURES

The disclosure may be more completely understood in consideration of the following detailed description of various embodiments of the disclosure in connection with the accompanying Figures, in which:

FIG. 1 is a table displaying results from the clinical treatment of Example 1 where secondary endpoints for hearing loss were measured in human subjects.

FIG. 2 is a table displaying results from the clinical treatment of Example 1 where secondary endpoints for hearing loss were measured in human subjects.

FIG. 3 is a table displaying results from the clinical treatment of Example 1 where secondary endpoints for hearing loss were measured in human subjects. The secondary endpoints measured include: the severity of sensorineural hearing loss using pure-tone audiometry (PTA), speech-discrimination using Words-in-Noise Test (WINT) before, during, and after treatment, the severity of tinnitus using the Tinnitus Functional Index (TFI) and Tinnitus Loudness (TL) before, during, and after treatment, and the severity of vertigo using the Vertigo Symptoms Scale (VSS, short form) before, during, and after treatment.

DETAILED DESCRIPTION

In various embodiments, the present disclosure provides for methods for treating, preventing, and/or ameliorating MD and/or endolymphatic hydrops comprising administering a therapeutically effective amount of a composition comprising ebselen.

A particular embodiment in the present disclosure relates to methods and compositions useful for treating, preventing, and/or ameliorating MD and/or endolymphatic hydrops, said composition comprising a combination of at least two compounds, the first compound being ebselen and the one or more other compounds are glutathione peroxidase modulator or mimic compound(s).

Representative compounds of the novel combination are described throughout the specification and claims.

In some embodiments, a glutathione peroxidase modulator comprises a compound selected from the group consisting of glutathione peroxidase mimic compounds, glutathione, glutathione prodrugs, and cysteine prodrugs.

In some embodiments, a representative compound of a glutathione peroxidase mimic compound comprises ebselen, (2-phenyl-1,2-benzisoselenazol-3(2H)-one) with an empirical formula $C_{13}H_9NOSe$, molecular weight 274.2 and a formula of:

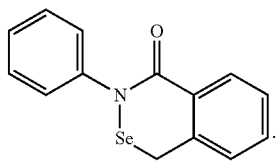 [SMILES: O=C1c2ccccc2C[Se]N1c1ccccc1]

In some embodiments, glutathione peroxidase mimic compounds comprise 2,2'-diseleno-bis-β-cyclodextrin and 6A,6B-diseleninic acid-6A',6B'-selenium bridged (3-cyclodextrin.

Glutathione peroxidase modulators or mimics, like glutathione peroxidase, reduce reactive oxygen species by the binding of free radicals to its Se moiety. By reacting with glutathione, glutathione peroxidase mimics limit free radical toxicity, thus exhibiting strong activity against peroxynitrite. Ebselen, a glutathione peroxidase mimic, reduces cytochrome C release from mitochondria and nuclear damage during lipid peroxidation, thus attenuating neuronal apoptosis associated with oxidative stress. Agents that reduce the activity of reactive oxygen species can ameliorate the deleterious effects of heightened oxidative stress and diseases caused by such stress, including but not limited to other neurologic diseases or disorders, and associated symptoms or complications thereof.

In some embodiments, representative glutathione prodrugs comprise compounds of the formula:

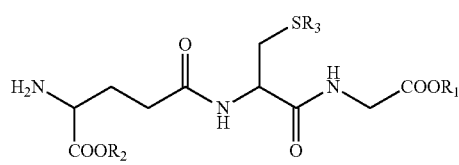

wherein
  $R_1$ is H, methyl, ethyl, or isopropyl;
  $R_2$ is H, or ethyl; and
  $R_3$ is H, acetyl, phenylacetyl,

In some embodiments, a representative cysteine prodrug comprises N-acetyl cysteine (NAC) with a formula of:

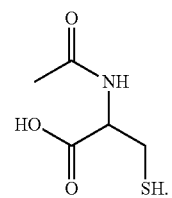

Some embodiments of cysteine prodrugs comprise N,N'-diacetyl-cysteine, N-acetyl cysteine amide, NAC esters (alkyl esters, glycolamide esters and acycloxymethyl esters), S-allyl cysteine, S-methyl cysteine, S-ethyl cysteine, S-propyl cysteine, or compounds of the formula:

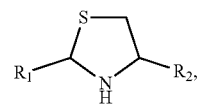

wherein
  $R_1$ is H, oxo, methyl, ethyl, n-propyl, n-pentyl, phenyl, —$(CHOH)_nCH_2OH$ and
wherein n is 1-5, or

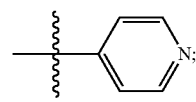

and
  $R_2$ is H or —COOH.

Some embodiments of cysteine prodrugs comprise 2-substituted thiazolidine-4-carboxylic acids with aldose monosaccharides, such as glyceraldehyde, arabinose, lyxose, ribose, xylose, galactose, glucose, and mannose.

Another aspect of the present disclosure features a pharmaceutical composition comprising a combination of glutathione peroxidase modulator or mimic compounds and at least one pharmaceutically acceptable carrier.

The present disclosure further features a process for making a pharmaceutical composition comprising admixing any of the compounds of the novel combination and a pharmaceutically acceptable carrier.

In a further embodiment, a method for treating or ameliorating MD and/or endolymphatic hydrops in a subject in need thereof comprises administering to the subject a therapeutically effective amount of a composition comprising ebselen or a combination of ebselen and one or more other glutathione peroxidase modulator or mimic compounds, wherein the therapeutically effective amount of each compound in the combination is from about 0.1 mg/dose to about 5 g/dose. In particular, the therapeutically effective amount of each compound in the composition is from about 0.5 mg/dose to about 1000 mg/dose. More particularly, the therapeutically effective amount of each compound in the composition is from about 1 mg/dose to about 100 mg/dose. In a further embodiment, the number of doses per day of the composition is from 1 to 3 doses. In a further embodiment, the therapeutically effective amount of each compound in the composition is from about 0.001 mg/kg/day to about 30 mg/kg/day. More particularly, the therapeutically effective amount of each compound in the composition is from about 0.01 mg/kg/day to about 2 mg/kg/day.

In a further embodiment, a method for preventing or inhibiting the progression of MD and/or endolymphatic hydrops in a subject in need thereof comprises administering to the subject a therapeutically effective amount of a composition comprising ebselen or a combination of ebselen and one or more other glutathione peroxidase modulator or mimic compounds, wherein the therapeutically effective amount of each compound in the combination is from about 0.1 mg/dose to about 5 g/dose. In particular, the therapeutically effective amount of each compound in the composition is from about 0.5 mg/dose to about 1000 mg/dose. More particularly, the therapeutically effective amount of each compound in the composition is from about 1 mg/dose to about 100 mg/dose. In a further embodiment, the number of doses per day of the composition is from 1 to 3 doses. In a further embodiment, the therapeutically effective amount of each compound in the composition is from about 0.001 mg/kg/day to about 30 mg/kg/day. More particularly, the therapeutically effective amount of each compound in the composition is from about 0.01 mg/kg/day to about 2 mg/kg/day.

Definitions/Terms

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used. Terms used in the claims and specification are defined as set forth below unless otherwise specified or by their usage throughout this disclosure.

Methods are known in the art for determining effective doses for therapeutic and prophylactic purposes for the disclosed pharmaceutical compositions or the disclosed drug combinations, whether or not formulated in the same composition. For therapeutic purposes, the term "therapeutically effective amount" as used herein, means that amount of each active compound or pharmaceutical agent, alone or in combination, that elicits the biological or medicinal response in a tissue system, animal or human that is being sought by a researcher, veterinarian, medical doctor or other clinician, which includes alleviation of the symptoms of the disease or disorder being treated. For prophylactic purposes (i.e., inhibiting the onset or progression of a disorder), the term "therapeutically effective amount" refers to that amount of each active compound or pharmaceutical agent, alone or in combination, that treats or inhibits in a subject the onset or progression of a disorder as being sought by a researcher, veterinarian, medical doctor or other clinician. Thus, the present disclosure provides combinations of two or more drugs wherein, for example, (a) each drug is administered in an independently therapeutically or prophylactically effective amount; (b) at least one drug in the combination is administered in an amount that is sub-therapeutic or sub-prophylactic if administered alone, but is therapeutic or prophylactic when administered in combination with the second or additional drugs according to the disclosure; or (c) both (or more) drugs are administered in an amount that is sub-therapeutic or sub-prophylactic if administered alone, but are therapeutic or prophylactic when administered together.

The term "Meniere's disease" refers to a disease or disorder, progressive or not, of the inner ear. The "classic" presentation of Meniere's is vertigo, hearing loss, and tinnitus. Herein, the term Meniere's disease is not to be constrained to be interpreted as a condition or disorder which is limited to only those which have all three of the aforementioned symptoms. Rather, MD is taken to be a disorder which is diagnosed as described in Example 1.

The term "endolymphatic hydrops" refers to the swelling of the endolymphatic compartment due to an accumulation of endolymphatic fluid in the ear.

The term "pharmaceutically acceptable salt" refers to non-toxic pharmaceutically acceptable salts (Ref. International J. Pharm., 1986, 33, 201-217; J. Pharm. Sci., 1997 (January), 66, 1, 1). Other salts well known to those in the art may, however, be useful in the preparation of compounds according to this disclosure or of their pharmaceutically acceptable salts. Representative organic or inorganic acids include, but are not limited to, hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Representative organic or inorganic bases include, but are not limited to, basic or cationic salts such as benzathine, chloroprocaine, choline, diethanolamine, ethylenediamine, meglumine, procaine, aluminum, calcium, lithium, magnesium, potassium, sodium and zinc.

The term "composition" is intended to encompass a product comprising the specified ingredients in the specified amounts, as well as any product which results, directly or indirectly, from combinations of the specified ingredients in the specified amounts.

The term "subject" encompasses an organism, an animal, including a mammal, human or non-human, male or female, who is the object of treatment, observation, clinical trial or experiment. The subject can be a human patient. The term "human" generally refers to Homo sapiens. The term "mammal" as used herein includes but is not limited to a human, non-human primate, mouse, rat, guinea pig, chinchilla and monkey. Mammals other than humans can be advantageously used as subjects that represent animal models of, e.g., hearing loss, schizophrenia, bipolar disorders, and/or any other psychotic disorder.

The term "statistically significant" is defined as the probability that a result is not caused by random chance.

The term "percent identity" or "percent sequence identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information website.

The term "statistically significant" is defined as the probability that a result is not caused by random chance.

It must be noted that, as used in the specification and the appended claims, the singular forms "a," "an," and "the" include plural referents unless the context clearly dictates otherwise.

Abbreviations or acronyms used in the throughout the specification include:
AEC: Adverse event checklist
ECochG: Electrocochleography
EOS: End of study
GSH: The reduced form of glutathione
GSSG: The oxidized form of glutathione
GPx: Glutathione peroxidases
GR: Glutathione reductase
NAC: N-acetyl-cysteine
NC: Normal controls
POC: Proof of concept
Redox: Reduction/oxidation
RNS: Reactive nitrogen species
ROS: Reactive oxygen species
SOD: Superoxide dismutase
h or hr (hour(s))
LCMS (high pressure liquid chromatography with mass spectrometer)
Me (methyl)
Mg (milligram)
rt or RT (room temperature)

Methods of Treatment

In Meniere's disease, accumulation of fluid begins in the inner ear and flows into other areas, causing damage. This accumulation of fluid is referred to as "hydrops". The membranes become dilated (stretched thin, like a balloon) when pressure increases and drainage is blocked. This may be related to swelling of the endolymphatic sac or other tissues in the vestibular system of the inner ear, which is responsible for the body's sense of balance. Meniere's symptoms vary. Not all sufferers experience the same symptoms at the same time.

Several preclinical animal studies have demonstrated the efficacy of glutathione peroxidase activity, and in particular, SPI-1005 (ebselen) at preventing and treating different acquired forms of sensorineural hearing loss. GPx1 is the dominant catalytic antioxidant enzyme in the mammalian inner ear, and its activity is decreased after ototoxic insult. Ebselen treatment has been shown to prevent or reverse the pathologic changes in the cochlea following noise- or ototoxin-induced injury.

In the cochlea, glutathione peroxidase (GPx) reacts with glutathione to limit free-radical toxicity. Also, glutathione peroxidase reduces reactive oxygen species by the binding of free radicals to its Se moiety. In this way, glutathione peroxidase is able to limit free radical toxicity from a number of cellular pathways. In normal functioning cells, GPx functions at near maximal capacity. However, GPx activity is severely diminished in the tissue in the cochlea of patients afflicted with MD and/or endolymphatic hydrops. Restoration of cochlear GPx activity might then subdue or even reverse the effects of these disorders and the accompanying inflammation Augmentation of GPx activity with the enzyme itself is not practical due to its large size and relative instability. However, small-molecule modulators and/or mimics for GPx activity have been synthesized and studied by a number of groups.

Ebselen [SPI-1005 or 2-phenyl-1,2-benzisoselenazol-3 (2H)-one] is a mimic of GPx activity and has strong activity against peroxynitrite (ONOO—), a super reactive oxygen species (ROS) formed by the combination of two free radicals, superoxide anion and nitric oxide (Noguchi et al., 1992; Noguchi et al., 1994). Ebselen reduces cytochrome-C release from mitochondria and nuclear damage during lipid peroxidation (Namura et al., 2001).

Thus, the present disclosure provides for methods of treating, preventing, and/or ameliorating MD and/or endolymphatic hydrops in a subject, the method comprising administering to the subject in need thereof a therapeutically effective amount of a composition comprising ebselen or a combination of ebselen and one or more other glutathione peroxidase modulator or mimic compounds.

In one aspect, the present disclosure provides for equalizing the pressure of the inner ear. The pressure system in the inner ear is very complex and sensitive to subtle variations in the static pressure of the middle ear. Concomitantly, pressure equalization for the inner ear is activated by the onset of changes in the middle ear. The pressure of the middle ear is dominated by gas exchange with middle ear tissue. Further, transient opening of the Eustachian tube also assists this pressure equilibrium. Gas exchange can be triggered by chewing or yawning, but it is also sensitive to altitude, e.g. when flying or diving (ear clearing). Meniere's patients can experience markedly worse pressure regulation in the middle ear. Ventilation (gas exchange) in the middle ear is affected by endolymphatic fluid level and is effective against the development and progression of Meniere's disease. Accordingly, agents which decrease the level of endolymphatic fluid influence the pathology preceding and immediately causing Meniere's disease. Thus, the present disclosure provides for methods of equalizing the pressure in the inner ear of a subject, the method comprising administering to the subject in need thereof a therapeutically effective amount of a composition comprising ebselen or a combination of ebselen and one or more other glutathione one or more other glutathione peroxidase modulator or mimic compounds.

In one aspect, the present disclosure provides for a method of reducing free radical production and/or inflammation in the cochlea tissue of the ear of a subject comprising administering to a subject in need thereof an effective amount of a composition comprising ebselen, and optionally, one or more other glutathione peroxidase modulator or mimic compounds. Specific free radical species include reactive oxygen species. More specifically, free radicals include, but are not limited to peroxynitrite, superoxide anion, nitric oxide, nitrotyrosine, and hydroxyl radicals.

In one aspect, the present disclosure provides for a method of treating, preventing, and/or ameliorating MD and/or endolymphatic hydrops in a subject, wherein the method restores or partially restores hearing loss or prevents hearing loss in the subject. The present disclosure provides for methods wherein the swelling of the endolymphatic compartment or other tissues in the vestibular system of the inner ear is reduced, ameliorated, arrested, or otherwise eliminated. The present disclosure provides for methods wherein reduced vertigo, and/or tinnitus is experienced by the subject. The present disclosure provides for a methods wherein the method reduces inflammation of tissue in the ear.

Further, in any of the methods described herein one or more GPx modulator or mimic compounds can be co-administered with ebselen in every single dose or intermittently, for example every other dose, or every third dose, or every fourth dose, or every fifth dose, or every sixth to twentieth dose. Of course, it is contemplated that the one or more GPx modulator or mimic compounds can be given on a regular interval which may or may not overlap with the dosing for ebselen. In such cases the GPx mimics or modulators can be given once every 4 hours, once every 6 hours, once every 12 hours, once daily, once every other day, once every third day, once every fifth day, once every week, once every ten days, once every two weeks, up to once every month.

In any of the methods described herein ebselen and the one or more GPx modulator or mimic compounds, or pharmaceutically acceptable salts, esters or prodrugs thereof, are administered orally, nasally, transdermally, pulmonary, inhalationally, buccally, sublingually, intra-aurally, intracochlearly, intratympanically, intraperintoneally, subcutaneously, intramuscularly, intravenously, rectally, intrapleurally, intrathecally and parenterally. The compound is administered orally. In another embodiment, the compound is administered by topical administration to the inner, middle, or outer ear.

In any of the methods described herein ebselen and the one or more GPx modulator or mimic compounds may be administered by various routes, including by parenteral, enteral, and topical administration routes. Methods of parenteral delivery include intra-muscular, intrathecal, intracerebroventricular, intra-arterial, subcutaneous, intramedullary, intravenous, or intranasal administration. In addition, compositions may contain suitable pharmaceutically acceptable carriers comprising excipients and other compounds that facilitate administration to a mammalian subject.

In any of the methods described herein, one or more prescription diuretic compounds may be used in combination with ebselen, or in combination with ebselen and one or more other glutathione peroxidase modulator or mimic compounds to make a composition useful for administration to a subject.

Compounds

Representative compounds of the present disclosure are described throughout the specification and claims.

A representative compound of glutathione peroxidase (GPx) mimics includes ebselen, (2-Phenyl-1,2-benzisoselenazol-3(2H)-one) with empirical formula $C_{13}H_9NOSe$, molecular weight 274.2 and a formula of:

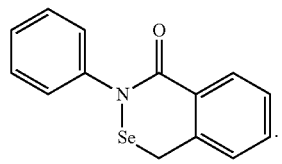 [SMILES: O=C1c2ccccc2C[Se]N1c1ccccc1]

In some embodiments, ebselen is the only active ingredient administered in a formulation. Ebselen is slightly soluble in aqueous solutions at 25° Celsius. Ebselen acts as a catalyst and is not consumed during detoxification reactions (Muller et. al, 1988). An embodiment of an ebselen formulation is >99% pure as confirmed by HPLC. The synthesis of this formulation is provided by Rhodia Pharma Solutions and includes capsules that are hermetically sealed in blister packs. Each capsule contains 200 mg the ebselen formulation or SPI-1000 (placebo).

Other representative compounds of glutathione peroxidase (GPx) mimics include 2,2'-diseleno-bis-β-cyclodextrin and 6A,6B-diseleninic acid-6A',6B'-selenium bridged (3-cyclodextrin.

Representative compounds of the GPx modulator compound in the combination include glutathione (GSH), glutathione prodrugs listed in Table 1, and cysteine prodrugs listed in Table 2.

TABLE 1

| glutathione prodrugs | | |
|---|---|---|
| STRUCTURE | NAME | NO. |
| H₂N-[structure with COOH, SH, O, N-H groups, methyl ester] | 1 | $N^5$-((R)-3-mercapto-1-((2-methoxy-2-oxoethyl)-amino)-1-oxopropan-2-yl)-L-glutamine |

TABLE 1-continued glutathione prodrugs

| STRUCTURE | NAME | NO. |
|---|---|---|
| (structure) | 2 | $N^5$-((R)-1-((2-ethoxy-2-oxoethyl)-amino)-3-mercapto-1-oxopropan-2-yl)-L-glutamine |
| (structure) | 3 | ethyl $N^5$-((R)-1-((2-ethoxy-2-oxoethyl)amino)-3-mercapto-1-oxopropan-2-yl)-L-glutamiuate |
| (structure) | 4 | $N^5$-((R)-1-((2-isopropoxy-2-oxoethyl)amino)-3-mercapto-1-oxopropan-2-yl)-L-glutamine |
| (structure) | 5 | $N^5$-((R)-3-(acetylthio)-1-((carboxymethyl)amino)-1-oxopropan-2-yl)-L-glutamine |
| (structure) | 6 | $N^5$-((R)-3-(benzoylthio)-1-((carboxymethyl)amino)-1-oxopropan-2-yl)-L-glutamine |
| (structure) | 7 | $N^5$-((R)-3-(((R)-2-amino-2-carboxyethyl)disulfanyl)-1-((carboxymethyl)amino)-1-oxopropan-2-yl)-L-glutamine |
| (structure) | 8 | 2-(((R)-2-((S)-4-amino-4-carboxybutanamido)-3-((carboxymethyl)amino)-3-oxopropyl)thio)succinic acid |

TABLE 2

| cysteine prodrugs | | |
|---|---|---|
| STRUCTURE | NO. | NAME |
| (structure) | 1 | N-acetyl cysteine |
| (structure) | 2 | N,N'-diacetyl cysteine |
| (structure) | 3 | N-acetyl cysteine amide |
| (structure) | 4 | N-acetyl cysteine alkyl esters |
| (structure) | 5 | N-acetyl cysteine glycolamide esters |
| (structure) | 6 | N-acetyl cysteine acycloxymethyl esters |
| (structure) | 7 | S-allyl cysteine |
| (structure) | 8 | S-methyl cysteine |
| (structure) | 9 | S-ethyl cysteine |
| (structure) | 10 | S-propyl cysteine |
| (structure) | 11 | (R)-thiazolidine-4-carboxylic acid |
| (structure) | 12 | (4R)-2-methylthiazolidine-4-carboxylic acid |
| (structure) | 13 | (4R)-2-ethylthiazolidine-4-carboxylic acid |
| (structure) | 14 | (4R)-2-propylthiazolidine-4-carboxylic acid |
| (structure) | 15 | (4R)-2-pentylthiazolidine-4-carboxylic acid |
| (structure) | 16 | (4R)-2-phenylthiazolidine-4-carboxylic acid |
| (structure) | 17 | (4R)-2-(pyridin-4-yl)thiazolidine-4-carboxylic acid |
| (structure) | 18 | (R)-2-oxothiazolidine-4-carboxylic acid |

TABLE 2-continued cysteine prodrugs

| STRUCTURE | NO. | NAME |
|---|---|---|
| HO-[CH(OH)]$_{n=1...5}$-[thiazolidine with S, NH, COOH] | 19 | For n = 3 (RibCys): 2(R,S)-D-ribo-(1',2',3',4'-tetrahydroxybutyl)-thiazolidine-4(R)-carboxylic acid |
| HO-[CH(OH)]$_{n=1...5}$-[thiazolidine with S, NH, H] | 20 | For n = 3 (RibCyst): 2(R,S)-D-ribo-(1',2',3',4'-tetrahydroxybutyl)-thiazolidine |

Some other embodiments of cysteine prodrugs include 2-substituted thiazolidine-4-carboxylic acids with aldose monosaccharides, such as glyceraldehyde, arabinose, lyxose, ribose, xylose, galactose, glucose, and mannose.

The disclosure provides for one or more diuretic compounds. Diuretics are medications which treat high blood pressure, heart disease and certain kinds of kidney or liver disease. They stimulate the kidneys to remove water from the body. These compounds are well-known in the art and generally come in three classes: thiazide diuretic, potassium-sparing, and loop-acting diuretics. Examples of compounds which are diuretic compounds include, but are not limited to, Aquatensen (methyclothiazide), Diucardin (hydroflumethiazide), Diulo (metolazone), Diuril (chlorothiazide), Enduron (methyclothiazide), Esidrix (hydrochlorothiazide), Hydrochlor (hydrochlorothiazide), Hydro-D (hydrochlorothiazide), HydroDIURIL (hydrochlorothiazide), Hydromox (quinethazone), Hygroton (chlorthalidone), Metahydrin (trichlormethiazide), Microzide (hydrochlorothiazide), Mykrox (metolazone), Naqua (trichlormethiazide), Naturetin (bendroflumethiazide), Oretic (hydrochlorothiazide), Renese (polythiazide), Saluron (hydroflumethiazide), Thalitone (chlorthalidone), Trichlorex (trichlormethiazide), Zaroxolyn (metolazone), Aldactone (spironolactone), Dyrenium (triamterene), Midamor (amiloride), Bumex (bumetanide), Demadex (torsemide), Edecrin (ethacrynic acid), and Lasix (furosemide), Myrosemide (furosemide). Prescription diuretic compounds can be obtained commercially.

In one aspect, the disclosure provides for glutathione peroxidase (GPx) modulators or mimics including, but not limited to, 2-phenyl-1,2-benzoisoselenazol-3(2H)-one (ebselen); 6A,6B-diseleninic acid-6A',6B'-selenium bridged β-cyclodextrin (6-diSeCD); and 2,2'-diseleno-bis-Beta-cyclodextrin (2-diSeCD).

In one aspect, the disclosure provides for amino acids or peptides which have at least 90%, more preferably 95%, still yet more preferably 98%, still yet more preferably 99%, and still yet more preferably 100 percent sequence identity to the amino acids or peptides disclosed herein.

Where the compounds according to this disclosure have at least one chiral center, they may accordingly exist as enantiomers. Where the compounds possess two or more chiral centers, they may additionally exist as diastereomers. Where the processes for the preparation of the compounds according to the disclosure give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, geometric isomers, and enantiomers thereof are encompassed within the scope of the present disclosure.

Furthermore, some of the crystalline forms for the compounds may exist as polymorphs and as such are intended to be included in the present disclosure. In addition, some of the compounds may form solvates with water (i.e., hydrates) or common organic solvents, and such solvates are also intended to be encompassed within the scope of this disclosure.

In one aspect, ebselen alone, or in combination with one or more GPx modulators or mimics or one or more prescription diuretic compounds, may be used to make a pharmaceutical composition by mixing the compound(s) with one or more pharmaceutical adjuvants and/or excipients.

Synthesis of the Compounds

In general, ebselen and GPx compounds of the present disclosure are commercially available, but have not been approved as prescription medications. Alternatively, ebselen and GPx modulators and mimics as described herein have been made or synthesized in U.S. Pat. Nos. 5,008,394; 5,399,573; International Patent Publication Nos. WO2010/074992, WO2013/016727; and China Patent Application No. 201410299898 and U.S. patent application Ser. No. 10/750,005, which are hereby incorporated in their entirety. Any necessary modifications to these compounds, such as one or more organic functional group or protecting group conversions to make, for example, the requisite R groups for the compound formulas disclosed herein, can be readily made by the skilled artisan by organic synthetic techniques described in T. W. Greene and P. G. M. Wuts, *Protecting Groups in Organic Synthesis*, Third Edition, Wiley, New York, 1999.

General Administration, Formulation, and Dosages

The present compounds are GPx modulators or mimics and are therefore useful in treating, preventing, or inhibiting the progression of MD and/or endolymphatic hydrops.

An embodiment features a method for treating a subject with MD and/or endolymphatic hydrops, said method comprising administering to the subject in need thereof a therapeutically effective amount of a pharmaceutical composition comprising one or more compounds disclosed herein.

Embodiments also include prodrugs of the compounds disclosed herein. In general, such prodrugs will be functional derivatives of the compounds which are readily convertible in vivo into the required compound. Thus, in the methods of treatment of the present disclosure, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundara, Elsevier, 1985.

Some of the crystalline forms for the compounds may exist as polymorphs and as such are intended to be included in the present disclosure. In addition, some of the compounds may form solvates with water (i.e., hydrates) or common organic solvents, and such solvates are intended to be encompassed by some embodiments.

Where the processes for the preparation of the compounds as disclosed herein give rise to mixtures of stereoisomers, these isomers may be separated by conventional techniques such as preparative chromatography. The compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. It is to be understood that all stereoisomers, racemic mixtures, diastereomers, cis-trans isomers, and enantiomers thereof are encompassed by some embodiments.

Dosages

Those of skill in the treatment of MD and/or endolymphatic hydrops can determine the effective daily amount from the test results presented hereinafter and other information. The exact dosage and frequency of administration depends on the particular compound of disclosure used, the particular condition being treated, the severity of the condition being treated, the age, weight and general physical condition of the particular patient as well as other medication the patient may be taking, as is well known to those skilled in the art. Furthermore, it is evident that said effective daily amount may be lowered or increased depending on the response of the treated patient and/or depending on the evaluation of the physician prescribing the compounds of the instant disclosure. The effective daily amount ranges mentioned herein are therefore only guidelines in practicing the present disclosure.

For the methods for the treatment of MD and/or endolymphatic hydrops described herein using any of the compounds as disclosed herein, the dosage form will contain a pharmaceutically acceptable carrier containing between from about 0.1 mg to about 5000 mg; particularly from about 0.5 mg to about 1000 mg; and, more particularly, from about 1 mg to about 100 mg of the compound, and may be constituted into any form suitable for the mode of administration selected. The dosages, however, may be varied depending upon the requirement of the subjects, the severity of the condition being treated and the compound being employed. The use of either daily administration or post-periodic dosing may be employed.

The pharmaceutical compositions herein will contain, per unit dosage unit, e.g., tablet, capsule, powder, injection, suppository, teaspoonful and the like, of from about 0.001 mg/kg/day to about 10 mg/kg/day (particularly from about 0.01 mg/kg/day to about 1 mg/kg/day; and, more particularly, from about 0.1 mg/kg/day to about 0.5 mg/kg/day) and may be given at a dosage of from about 0.001 mg/kg/day to about 30 mg/kg/day (particularly from about 0.01 mg/kg/day to about 2 mg/kg/day, more particularly from about 0.1 mg/kg/day to about 1 mg/kg/day and even more particularly from about 0.5 mg/kg/day to about 1 mg/kg/day).

These compositions are in unit dosage forms from such as tablets, pills, capsules, dry powders for reconstitution or inhalation, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, dry powder inhaler or other inhalation or insufflation means. Alternatively, the composition may be presented in a form suitable for once-weekly or once-monthlyadministration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, anti-adherents and gildants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol, sorbitol, microcrystalline cellulose (i.e. AVICEL™ microcrystalline cellulose available from FMC Corp.), dicalcium phosphate, calcium sulfate dihydrate, calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethylcellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose [i.e. TYLOSE™ available from Hoechst Celanese], polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin, and tragacanth gum), cross-linked polyvinylpyrrolidone and the like. Suitable lubricants and anti-adherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable gildants include, but are not limited to, talc, cornstarch, silica (i.e. CAB-O-SIL™ silica available from Cabot, SYLOID™ silica available from W. R. Grace/Davison, and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active form of the present disclosure, or a pharmaceutically acceptable salt thereof. Generally the preformulation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 5000 mg of the active ingredient of the present disclosure. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate, cellulose acetate trimetllitate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetylstearyl alcohol, and the like), esters of fatty acids metallic soaps, and other acceptable materials that can be used to granulate, coat, entrap or otherwise limit the solubility of an active ingredient to achieve a prolonged or sustained release product.

The liquid forms in which the novel compositions disclosed herein may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth, and xanthan gum, cellulosics such as sodium carboxymethylcellulose, methylcellulose, hydroxymethylcellulose, hydroxyethylcellulose, hydroxypropyl cellulose and hydroxypropyl methylcellulose, and combinations thereof, synthetic polymers such as polyvinyl pyrrolidone, carbomer (i.e. carboxypolymethylene), and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agents include pharmaceutical grade lecithins. Suitable flocculating agent include but are not limited to simple neutral electrolytes (i.e. sodium chloride, potassium, chloride, and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfactants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds disclosed herein can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds disclosed herein can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

The daily dose of a pharmaceutical composition disclosed herein may be varied over a wide range from about 0.1 mg to about 5000 mg; preferably, the dose will be in the range of from about 1 mg to about 100 mg per day for an average human. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250, 500, 750, 1000, 1250, 1500, 1750, 2000, 2500, or 3000 milligrams of the active ingredient for the symptomatic adjustment of the dosage to the subject to be treated. Advantageously, a compound of the present disclosure may be administered in a single daily dose or the total daily dosage may be administered in divided doses of two, three or four times daily.

The therapeutically effective dose for active compounds disclosed herein or a pharmaceutical composition thereof may vary according to the desired effect. Therefore, optimal dosages to be administered may be readily determined by those skilled in the art, and may vary with the particular compound used, the mode of administration, the strength of the preparation, and the advancement of the disease condition. In addition, factors associated with the particular subject being treated, including subject age, weight, diet and time of administration, will result in the need to adjust the dose to an appropriate therapeutic level. The above dosages are thus exemplary of the average case. There can, of course, be individual instances where higher or lower dosage ranges are merited, and such are within the scope of this disclosure.

Compounds disclosed herein may be administered in any of the foregoing compositions and dosage regimens or by means of those compositions and dosage regimens established in the art whenever use of the compounds disclosed herein as GPx modulators or mimic is required for a subject in need thereof.

Formulations

To prepare the pharmaceutical compositions disclosed herein, one or more compounds disclosed herein or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in The Handbook of Pharmaceutical Excipients, published by the American Pharmaceutical Association and the Pharmaceutical Society of Great Britain.

The compounds of the present disclosure may be formulated into various pharmaceutical forms for administration purposes. Methods of formulating pharmaceutical compositions have been described in numerous publications such as Pharmaceutical Dosage Forms: Tablets, Second Edition, Revised and Expanded, Volumes 1-3, edited by Lieberman et al; Pharmaceutical Dosage Forms: Parenteral Medications, Volumes 1-2, edited by Avis et al; and Pharmaceutical Dosage Forms: Disperse Systems, Volumes 1-2, edited by Lieberman et al; published by Marcel Dekker, Inc.

Ebselen formulations, in form of a capsule, were prepared for below examples that investigated ebselen as a novel therapeutic for MD and/or endolymphatic hydrops. Ebselen may or may not be the only active ingredient in the formulations, and may act as a catalyst for biochemical reactions in which case it is not being consumed during detoxification reactions. The formulation was >99% pure as determined by HPLC. The capsules were hermetically sealed in blister packs. Each capsule contained 200 mg of ebselen that possesses a low toxicity because of its unique structure stability. Its selenium (Se) moiety is not liberated during biotransformation and therefore does not enter selenium metabolism. It is possible that in the process of manufacture, there was remaining unbound selenium present. The manufacturing criterion is that each capsule contains less than 1 microgram of inorganic selenium. In humans, selenium toxicity, or selenosis, can occur following chronic ingestion of high quantities of selenium. The Recommended Daily Allowance (RDA) of selenium for adults is 55 microgram per day. Dosage is adjusted to result in the total selenium exposure being significantly less than RDA which is monitored during the study.

EXAMPLES

Below are examples of specific embodiments for carrying out the present disclosure. The examples are offered for illustrative purposes only, and are not intended to limit the scope of the present disclosure in any way. Efforts have been made to ensure accuracy with respect to numbers used (e.g., amounts, temperatures, etc.), but some experimental error and deviation should, of course, be allowed for.

The practice of the present disclosure will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* $3^{rd}$ Ed. (Plenum Press) Vols A and B (1992).

Example 1: Clinical Treatment of Meniere's Disease Patients

Introduction

Meniere's disease (MD) is defined as a triad of episodic vertigo, hearing loss and tinnitus. Aural pressure or fullness is often reported and most auditory and vestibular symptoms fluctuate in frequency and intensity. Endolymphatic hydrops is a swelling of the endolymphatic compartment of the inner ear and has been directly linked to MD. Most MD patients are medically managed using a low-salt diet and/or a thiazide diuretic with limited success. After an acute phase where vertigo is the most common feature, the chronic phase emerges, where hearing loss and tinnitus become the most common features, although disequilibrium is often reported.

MD Criteria

AAO-HNS 1995 Diagnostic Criteria for Meniere's Disease

Possible Meniere's Disease
  Episodic vertigo of the Meniere's type without documented hearing loss, or
  Sensorineural hearing loss, fluctuating or fixed, with dysequilibrium but without definitive episodes Other causes excluded
Probable Meniere's Disease
  One definitive episode of vertigo
  Audiometrically documented hearing loss on at least one occasion
  Tinnitus or aural fullness in the treated ear
  Other causes excluded
Definite Meniere's Disease
  Two or more definitive spontaneous episodes of vertigo 20 minutes or longer Audiometrically documented hearing loss on at least one occasion
  Tinnitus or aural fullness in the treated ear
  Other cases excluded
Certain Meniere's Disease
  Definite Meniere's disease, plus histopathologic confirmation
  American Academy of Otolaryngology-Head and Neck Foundation, Inc. Committee on Hearing and Equilibrium guidelines for the diagnosis and evaluation of therapy in Meniere's disease. *Otolaryngol Head Neck Surg.* 1995 September; 113 (3):181-5.

Thorp M A, Shehab Z P, Bance M L, Rutka J A; AAO-HNS Committee on Hearing and Equilibrium. The AAO-HNS Committee on Hearing and Equilibrium guidelines for the diagnosis and evaluation of therapy in Meniere's disease: have they been applied in the published literature of the last decade? *Clin Otolaryngol Allied Sci.* 2003 Jun; 28 (3):173-6.

The general approach for the investigation of the safety and efficacy of SPI-1005 for Meniere's disease is conducting this phase 1b, safety, pharmacokinetic and pharmacodynamic study in 40 adults with Meniere's disease. The study is evaluating escalating doses of SPI-1005 at 200, 400 or 600 mg po BID versus placebo for twenty-one days for impact on pure-tone audiometry, speech discrimination, electrocochleography, and patient-reported outcomes using validated questionnaires for assessing vertigo and tinnitus (Hornibrook, et al., 2012; Meikle, et al., 2011; Yardley, et al., 2004). This study is ongoing and being conducted in compliance with the protocol, Good Clinical Practice (GCP) and the applicable regulatory requirements.

Study Objectives

The objectives of this study are to evaluate the safety, PK and PD of three dose levels of SPI-1005 which are being given for 21 days compared to placebo in patients with Meniere's disease.

Primary Objective

The safety and tolerability of SPI-1005 is being determined by examining the toxicities and adverse events that are attributable to treatment. The safety parameters include an evaluation of the clinical signs and symptoms from the history and physical exam; vital signs, the incidence of adverse events; and abnormal laboratory findings.

Secondary Objectives

The secondary objectives of this study are to determine the pharmacokinetics at each dose level of SPI-1005; severity of sensorineural hearing loss using pure-tone audiometry and speech-discrimination testing using Words-in-Noise Test (WINT) before, during, and after treatment; severity of vertigo using the Vertigo Symptoms Scale (VSS, short form) before, during, and after treatment; severity of tinnitus using the Tinnitus Functional Index (TFI) before, during, and after treatment; and pharmacodynamic response using electrocochleography (ECochG) before, during, and after treatment.

Study Design

Study participants were been randomized to SPI-1005 or placebo in this double-blind, dose-escalation study to evaluate its safety and preliminary efficacy. Patients, aged 19-70 years, with probable or definite Meniere's disease have undergone baseline testing to have their severity of sensorineural hearing loss, tinnitus and vertigo determined before the start of study treatment (see Table 3: Schedule of Assessments).

Before, during, and for 28 days after administration of SPI-1005, patients were evaluated for safety by history, physical examination, vital signs and blood tests (complete blood count [CBC], Chemistry-20 [Chem-20]). Peak and trough plasma levels of ebselen and its major metabolite were determined using liquid chromatography-mass spectrometry (LCMS) at certain time points. Additionally, plasma was analyzed by High Performance Liquid Chromatography-Inductively Coupled Plasma-Mass Spectrometry (HPLC-ICP-MS) for total selenium at the corresponding time points. Patients were monitored for adverse events at each clinic visit. Female patients received pregnancy testing, and those found to be pregnant were excluded or discontinued from the study and monitored for adverse events. Safety monitoring was extended for four weeks after completion of treatment.

The effect of SPI-1005 on hearing and vertigo was evaluated at baseline, at the end of 21 days of treatment and 28 days after completing treatment. Tinnitus was evaluated at baseline, weekly during treatment, and 7 and 28 days after treatment. Hearing was evaluated using pure-tone audiometric testing at 0.25, 0.5, 1, 2, 3, 4, 6, and 8 kHz, and speech discrimination using the WINT at 24, 20, 16, 12, 8, 4, and 0 Signal-to-Noise ratio (SNR). The severity of vertigo was assessed using the VSS. The severity of tinnitus was assessed using the TFI. In addition, ECochG was conducted at baseline, at the end of treatment and 28 days after completing treatment in order to measure the pharmacodynamic response.

Description of Treatment

Compound

SPI-1005 is a proprietary formulation of the compound ebselen, consisting of gelatin capsules containing 200 mg of the active pharmaceutical ingredient ebselen and 150 mg of the excipients, microcrystalline cellulose, sodium croscarmellose, and magnesium stearate.

Dosing Levels

There were three dose levels: 200 mg, 400 mg, and 600 mg of SPI-1005.

Dosing Regimen

Patients were randomized to SPI-1005 or placebo in three successive dose-escalation cohorts: Cohort 1: 200 mg po BID (n=10) or placebo (n=3) for 21 days; Cohort 2: 400 mg po BID (n=10) or placebo (n=3) for 21 days; Cohort 3: 600 mg po BID (n=10) or placebo (n=4) for 21 days.

Each dose was administered as three capsules in the morning before eating and three capsules in the evening before eating. The three capsules include a combination of SPI-1005 and/or identical placebo capsules to provide the targeted dose level.

Dosage Form

1-size capsule contained either 200 mg of ebselen or matching placebo.

Manufacturer

SPI-1005 was manufactured by Catalent Pharma Solutions, Somerset, NJ.

Route of Administration

SPI-1005 (or matching placebo) was orally delivered.

Study Procedures

Duration of Treatment

Study treatment was administered over a 21-day period beginning on Study Day 1.

Duration of Study

Patients participated in this clinical trial for approximately seven to nine weeks beginning at baseline testing and continuing for four weeks beyond their final dose to allow for drug safety monitoring. A two-week window (Study Day -14 to -1) was allowed to complete baseline testing. Each patient had six clinical visits during the study (see Table 3, Schedule of Assessments).

The initial screening ocurred by telephone to obtain a brief history, review inclusion and exclusion criteria, discuss the informed consent form, explain remuneration for clinic visits and blood draws, and to schedule the first clinic visit if appropriate and agreeable.

Clinic Visit 1 (Day -14 to -1)

Informed consent for study participation was obtained before study evaluations were conducted. History and physical examination, vital signs, height/weight, blood tests (Chem-20, CBC) and urine pregnancy test were conducted up to 14 days prior to initiation of treatment (Study Day 1). Baseline symptoms and concomitant medications were recorded. Blood for total selenium level was obtained. Baseline hearing evaluation consisted of otoscopy, tympanometry, pure-tone audiometry at 0.25, 0.5, 1, 2, 3, 4, 6, and 8 kHz and speech discrimination using the WINT at 24, 20, 16, 12, 8, 4 and 0 SNR. Baseline vertigo was assessed using the VSS. Baseline tinnitus evaluation was conducted using the TFI. Baseline ECochG was performed.

Following receipt of informed consent, blood testing, history, physical examination, baseline audiometric testing, enrollment in the study, and verbal instructions about the protocol, each patient received a drug card containing capsules of SPI-1005 and/or placebo. The dispensing clinician recorded the Subject Identification Code, Date of Issue, and Card Number for each card issued. Patient was counseled to refrain from taking their morning dose on the morning of their next clinic visit prior to returning to clinic.

Clinic Visit 2 (Day 7, Before am Dose)

History and physical exam and vital signs were performed. Adverse events were recorded. Concomitant medications were recorded. Compliance with treatment was measured by patient history and pill count. Blood tests, including but not limited to Chem-20 and CBC, were conducted. Trough blood samples for total selenium and ebselen and its metabolite levels were drawn prior to the morning dose of study drug. Tinnitus evaluation was conducted using the TFI. Patient was counseled to refrain from taking their morning dose on the morning of their next clinic visit prior to returning to clinic.

Clinic Visit 3 (Day 14, Before am Dose)

History and physical exam and vital signs were performed. Adverse events were recorded. Concomitant medications were recorded. Compliance with treatment was measured by patient history and pill count. Trough blood samples for total selenium and ebselen and its metabolite levels were drawn prior to the morning dose of study drug. Tinnitus evaluation was conducted using the TFI. Patient was counseled to refrain from taking their morning dose on the morning of their next clinic visit prior to returning to clinic.

Clinic Visit 4 (Day 21, Before and After am Dose on Last Day of Dosing)

History and physical exam and vital signs were performed. Adverse events were recorded. Concomitant medications were recorded. Compliance with treatment was measured by patient history and pill count. Blood tests, including but not limited to Chem-20 and CBC, were conducted. Trough blood samples for total selenium and ebselen and its metabolite levels were drawn prior to the morning dose of study drug. Peak blood samples for total selenium and ebselen and its metabolite levels were drawn two hours after study drug administration. Hearing evaluation consisted of pure-tone audiometry at 0.25, 0.5, 1, 2, 3, 4, 6, and 8 kHz and speech discrimination using the WINT at 24, 20, 16, 12, 8, 4 and 0 SNR. Vertigo was assessed using the VSS. Tinnitus evaluation was conducted using the TFI. End-of-treatment ECochG is performed.

Clinic Visit 5 (Day 28, 7 Days After Last Dose of SPI-1005)

History and physical exam and vital signs were performed. Adverse events were recorded. Concomitant medications were recorded. Compliance with treatment was measured by patient history and final pill count. Blood samples for total selenium and ebselen and its metabolite levels were drawn. Tinnitus evaluation was conducted using the TFI.

Clinic Visit 6 (Day 49, 28 Days After Last Dose of SPI-1005)

History and physical exam and vital signs were performed. Adverse events were recorded. Concomitant medications were recorded. Compliance with treatment was measured by patient history and final pill count. Blood tests, including but not limited to Chem-20 and CBC, were conducted. Blood samples for total selenium and ebselen and its metabolite levels were drawn. Hearing evaluation consisted of pure-tone audiometry at 0.25, 0.5, 1, 2, 3, 4, 6, and 8 kHz and speech discrimination using the WINT at 24, 20, 16, 12, 8, 4 and 0 SNR. Vertigo was assessed using the VSS. Tinnitus evaluation was conducted using the TFI. Post-treatment ECochG was performed.

Assessment of Safety and Efficacy

Medical Evaluation

History and physical examinations, vital signs and analysis of lab reports were performed to evaluate the safety of SPI-1005. A licensed Medical Doctor (MD) or Physician Assistant (PA) performed physical examinations using standard clinical equipment at the appointed study intervals. Blood test results were analyzed according to currently established laboratory norms. Patients were asked about adverse events at each clinic visit.

Laboratory Testing

Blood testing was performed at specified intervals to evaluate the safety of SPI-1005. A qualified medical laboratory technician performed laboratory testing using standard equipment and established universal safety precautions for collecting and handling blood samples. Blood tests performed include CBC and Chem-20. Blood was collected and shipped to a designated CRO(s) to quantify ebselen, ebselen metabolite, and total selenium.

Audiometric Testing

Audiological evaluations were performed at specified intervals to evaluate the efficacy of SPI-1005. Tests included otoscopy, tympanometry, pure-tone audiometry, bone conduction and speech discrimination performed by physician or qualified audiologist (Wilson and Burks, 2005). ECochG was performed at specified intervals by a physician specialist. Patient-reported outcomes by self-administered questionnaire included the VSS (Yardley et al., 2004) and the TFI (Meikle et al., 2011). These were scored by study personnel.

Analyses

Multiple clinical assessments and analysis of auditory and vestibular function
  Pure tone audiometry and word recognition scores: Baseline, 21d tx, and 28d post-tx
    Hearing loss is typically unilateral and low frequency (0.25, 0.5 and 1 kHz)
      Significant hearing improvement ≥10 dB reduction from baseline
    Words in noise tests (WINT) 35 words under 7 different SNRs to each ear (0-35)
      Significant WINT improvement ≥10% increase from baseline
  Tinnitus Functional Index (TFI) : Baseline, and 7d, 14d and 21d tx, and 7d and 28d post-tx
    25 questions answered by patient regarding their tinnitus severity (0-100)
      Significant TFI improvement ≥10 pt reduction from baseline
    Tinnitus Loudness (TL) answered by patient on a visual analogue scale (0-10)
      Significant TL improvement ≥2 pt reduction from baseline
  Vertigo Symptom Scale (VSS): Baseline, 21d tx, and 28d post-tx
    15 questions answered by patient regarding their vertigo severity (0-60)
      Significant VSS improvement ≥6 pt reduction from baseline Statistical Analysis of Study Endpoints Adverse events were coded using MedDRA (Version 18.1 or higher) and summarized by each dose level (placebo, 200, 400 and 600 mg BID) for the number of adverse events. Comparisons were made between baseline, while on treatment, and 7-day and 28-day follow-up values.

Vital signs and clinical laboratory results were summarized for each dose level. Comparisons were made between baseline, on treatment, 7-day and 28-day follow-up values. Abnormal values were identified and categorized for severity.

Audiometric data were collected in the form of categorical and continuous variables. Categorical data were analyzed using the chi-square distribution. Continuous data were analyzed using mixed-effects multiple-repeated measures, and post-hoc analysis, when necessary, was adjusted using Bonferroni applications. Non-parametric tests included the Mann-Whitney U. Calculated p-values were considered statistically significant at or below an alpha value of 0.05. Backwards stepwise regression were used to determine the final model including only variables with significance at a 0.05 level. The sample size of 40 patients was sufficient to provide safety, PK and PD results to guide future dose selection.

Example 2: Clinical Treatment Data

Initial safety, auditory and vestibular findings
Oral dosing for 21 days is well tolerated with no adverse events due to study drug
Pure tone audiometry (PTA) and word recognition scores (WRS) show some agreement
  Improvements were as high as 35 dB in low frequency (0.25, 0.5, and 1 kHz) hearing
    Significant hearing improvement ≥10 dB in 60% of actives
    NO significant improvement in placebos has been observed
  Improvements were as high as 120% over baseline WRS
    Significant WINT improvement ≥10% increase in 35% of actives
    NO significant improvement in placebos has been observed
Both PTA/WINT improvements are significant and specific to actives vs placebos
Improvement in low frequency hearing may precede an improvement in WRS
Tinnitus Functional Index (TFI) and Tinnitus Loudness (TL) show some agreement
  Improvements in TFI score were as high as a 62 pt reduction (0-100)
    Significant TFI improvement ≥10 pt reduction in 40% of actives
    Significant TFI improvement in placebo is 50%
  Improvements in tinnitus loudness were as high as an 8 pt reduction (0-10)
    Significant TL improvement ≥2 pt reduction in 70% of actives
    Significant TFI improvement in placebo is 33%
Vertigo Symptom Scale (VSS)
  Improvements were as high as a 33 pt reduction (0-60)
    Significant VSS improvement ≥6 pt reduction in 55% of actives
    Significant VSS improvement in placebo is 33%
TL and VSS improvements are greater in actives than placebo
TFI, TL and VSS all show placebo effects Discussion of the Results Forty (40) adult volunteers fitting the AAO-HNS 1995 Criteria in the last 12 months, as described above, participated in the clinical treatment. The clinical results from a subset of twenty-six (26) of the forty (40) adult subjects are tabulated in FIGS. 1-3. Data produced by these first two cohorts demonstrate that administration of ebselen is safe and well tolerated since no significantly adverse events were observed. Furthermore, no drug-related adverse events have occurred.

The initial analysis of efficacy shows that ebselen achieved several secondary endpoints versus placebo.

Ebselen treatment showed clinically relevant improvements in hearing, tinnitus and vertigo across the two analyzed cohorts.

The data from this clinical treatment support the use of ebselen, and more generally, glutathione peroxidase (GPx)

modulators and mimics to limit free-radical damage, cochlear or vestibular inflammation. To conclude, GPx modulator, ebselen, demonstrated good clinical efficacy for treating, preventing, and/or ameliorating MD and/or endolymphatic hydrops in these cohorts.

All references, issued patents and patent applications cited within the body of the instant specification are hereby incorporated by reference in their entirety, for all purposes.

LIST OF REFERENCES

American Academy of Otolaryngology-Head and Neck Foundation. Committee on Hearing and Equilibrium guidelines for the diagnosis and evaluation of therapy in Meniere's disease. Otolaryngol Head Neck Surg. 1995; 113:181-5.

Hornibrook J, Kalin C, Lin E, et al. Transtympanic electrocochleography for the diagnosis of Meniere's disease. Int J Otolaryngol 2012; article 852714:1-11.

Kil J, Pierce C, Tran H, Gu R, Lynch ED. Ebselen treatment reduces noise-induced hearing loss via the mimicry and induction of glutathione peroxidase. Hearing Res 2007; 226:44-51.

Lee J E, Nakagawa T, Kim T S, Endo T, Shiga A, Iguchi F, Lee S H, Ito J. Role of reactive radicals in degeneration of the auditory system of mice following cisplatin treatment. Acta Otolaryngol. 2004 December; 124 (10):1131-5.

fLynch E D, Gu R, Pierce C, Kil J. Reduction of acute cisplatin ototoxicity and nephrotoxicity in rats by oral administration of allopurinol and ebselen. Hear Res. 2005 March; 201 (1-2): 81-9.

Meikle M B, Henry J A, Greist S E, et al. Tinnitus Functional Index: Development of a new clinical measure for chronic, intrusive tinnitus. Ear Hearing 2011; 33:153-176.

Müller A, Cadenas E, Graf P, Sies H. A novel biologically active seleno-organic compound-I. Glutathione peroxidase-like activity in vitro and antioxidant capacity of PZ51 (ebselen). Biochem Pharmacol 1984; (33):3235-9.

Müller A, Gabriel H, Sies H, Terlinden R, Fischer H, Romer A. A novel biologically active seleno-organic compound—VII. Biotransformation of ebselen in perfused rat liver. Biochem Pharmacol. 1988 Mar. 15; 37 (6): 1103-9.

Namura S, Nagata I, Takami S, Masayasu H, Kikuchi H. Ebselen reduces cytochrome c release from mitochondria and subsequent DNA fragmentation after transient focal cerebral ischemia in mice. Stroke 2001 August; 32 (8): 1906-11.

Noguchi N, Yoshida Y, Kaneda H, Yamamoto Y, Niki E. Action of ebselen as an antioxidant against lipid peroxidation. Biochem Pharmacol. 1992 Jul. 7; 44 (1):39-44.

Noguchi N, Gotoh N, Niki E. Effects of ebselen and probucol on oxidative modifications of lipid and protein of low density lipoprotein induced by free radicals. Biochim Biophys Acta. 1994 Jul. 14; 1213 (2):176-182.

Reiter R, Wendel A. Selenium and drug metabolism—II. Independence of glutathione peroxidase and reversibility of hepatic enzyme modulations in deficient mice. Biochem Pharmacol 1984 Jun. 15; 33 (12):1923-8.

Thorp M A, Shehab Z P, Bance M L, Rutka J A. AAO-HNS Committee on Hearing and Equilibrium. The AAO-HNS Committee on Hearing and Equilibrium guidelines for the diagnosis and evaluation of therapy in Meniere's disease: have they been applied in the published literature of the last decade? Clin Otolaryngol Allied Sci 2003; 28:173-6.

Wendel A, Fausel M, Safayhi H, Tiegs G, Otter R. A novel biologically active seleno-organic compound—II. Activity of PZ 51 in relation to glutathione peroxidase. Biochem Pharmacol 1984 October 15; 33 (20):3241-5.

Wilson R H, Burks Calif. Use of 35 words for evaluation of hearing loss in signal-to-noise babble ratio: A clinical protocol. JRRD 2005; 42:839-52.

Yardley L, Donovan-Hall M, Smith H E, Walsh B M, Mullee M, Bronstein A M. Effectiveness of primary care-based vestibular rehabilitation for chronic dizziness. Ann Intern Med 2004; 141:598-605.

I claim:

1. A method of treating Meniere's disease, comprising: administering to a human subject having Meniere's disease a therapeutically effective amount of ebselen or a pharmaceutically acceptable salt thereof.

2. The method of claim 1, wherein ebselen or the pharmaceutically acceptable salt thereof is administered orally.

3. The method of claim 2, wherein ebselen or the pharmaceutically acceptable salt thereof is ebselen.

4. The method of claim 3, wherein ebselen is administered at 1 to 3 doses per day.

5. The method of claim 4, wherein ebselen is administered twice per day (BID).

6. The method of claim 5, wherein the twice per day (BID) dose is 200, 400 or 600 mg of ebselen.

7. The method of claim 6, wherein the twice per day (BID) dose is 200 mg of ebselen.

8. The method of claim 6, wherein the twice per day (BID) dose is 400 mg of ebselen.

9. The method of claim 6, wherein ebselen is administered for 21 days or more.

10. The method of claim 1, wherein ebselen or the pharmaceutically acceptable salt thereof is formulated for oral administration in a solid dosage form.

11. The method of claim 10, wherein the solid dosage form is a capsule.

12. The method of claim 1, further comprising assessing the subject for one or more of hearing loss, tinnitus, and vertigo.

13. The method of claim 12, wherein the assessment is performed prior to treatment.

14. The method of claim 12, wherein the assessment is performed during and/or after the administration of ebselen or a pharmaceutically acceptable salt thereof.

15. The method of claim 12, wherein the assessment is performed using at least one technique selected from pure-tone audiometry, speech discrimination testing, and electrocochleography.

16. The method of claim 12, wherein vertigo in the subject is assessed using the Vertigo Symptoms Scale (VSS).

17. The method of claim 16, wherein the subject has a VSS score at least six (6) points below a baseline VSS score after treatment.

18. The method of claim 17, wherein the baseline VSS score is assessed prior to the subject receiving treatment.

19. The method of claim 12, wherein tinnitus in the subject is assessed using the Tinnitus Functional Index (TFI) or Tinnitus Handicap Inventory (THI).

20. The method of claim 12, wherein the subject is assessed to have an improved test score selected from Vertigo Symptoms Scale (VSS), Dizziness Handicap Inventory (DHI), Tinnitus Functional Index (TFI), and Tinnitus Handicap Inventory (THI) after treatment.

21. The method of claim 12, wherein after treatment the subject is assessed to have improvement of at least one of pure tone audiometry, speech discrimination test, and electrocochleography.

22. The method of claim 12, wherein after treatment the subject is assessed to have reduced hearing loss at multiple low frequencies.

23. The method of claim 22, wherein the multiple low frequencies are selected from 0.25 kHz, 0.5 kHz and 1 kHz.

24. The method of claim 12, wherein the subject is assessed to have reduced incidence of a Significant Threshold Shift of at least 10 dB from a baseline measurement after treatment.

25. A method of treating Meniere's disease, comprising:
    orally administering to a human subject having Meniere's disease 400 mg of ebselen twice per day (BID) for 21 days or more.

26. The method of claim 25, wherein after treatment the subject is assessed to have an improved test score selected from Vertigo Symptoms Scale (VSS), Dizziness Handicap Inventory (DHI), Tinnitus Functional Index (TFI), and Tinnitus Handicap Inventory (THI).

27. The method of claim 25, wherein after treatment the subject is assessed to have improvement of at least one of pure tone audiometry, speech discrimination test, and electrocochleography.

28. The method of claim 25, wherein after treatment the subject is assessed to have reduced hearing loss at multiple low frequencies.

29. The method of claim 1, wherein the ebselen or a pharmaceutically acceptable salt thereof is administered as a sole active ingredient.

* * * * *